(12) United States Patent
Yu et al.

(10) Patent No.: US 10,299,887 B2
(45) Date of Patent: May 28, 2019

(54) ATMOSPHERIC NON-THERMAL GAS PLASMA METHOD FOR DENTAL SURFACE TREATMENT

(75) Inventors: Qingsong Yu, Columbia, MO (US); Hao Li, Columbia, MO (US); Meng Chen, Columbia, MO (US)

(73) Assignees: Nanova, Inc., Columbia, MO (US); Curators of the University of Missouri Office of Intellectual Property Admin., Columbia, MO (US)

( * ) Notice: Subject to any disclaimer, the term of this patent is extended or adjusted under 35 U.S.C. 154(b) by 373 days.

(21) Appl. No.: 12/766,602

(22) Filed: Apr. 23, 2010

(65) Prior Publication Data

US 2010/0273129 A1    Oct. 28, 2010

Related U.S. Application Data

(60) Provisional application No. 61/214,450, filed on Apr. 23, 2009.

(51) Int. Cl.
*A61C 5/00* (2017.01)
*A61C 5/30* (2017.01)
*A61C 13/107* (2006.01)

(52) U.S. Cl.
CPC ................. *A61C 5/30* (2017.02); *A61C 5/00* (2013.01); *A61C 13/0001* (2013.01)

(58) Field of Classification Search
CPC . A61L 2/14; A61L 27/24; A61L 27/56; A61L 27/3839; A61K 6/00; A61K 6/0023; A61K 6/083; A61Q 11/00; A61C 5/00; H05H 2240/10; H05H 2240/20; A61B 2018/00452

USPC ................ 433/215–226; 315/111.21; 216/67
See application file for complete search history.

(56) References Cited

U.S. PATENT DOCUMENTS

| | | | |
|---|---|---|---|
| 5,249,964 A * | 10/1993 | Levy | 433/215 |
| 5,554,030 A * | 9/1996 | Ario et al. | 433/226 |
| 5,595,487 A * | 1/1997 | Ario et al. | 433/226 |
| 5,829,979 A * | 11/1998 | Kobashigawa et al. | 433/180 |
| 5,977,715 A * | 11/1999 | Li et al. | 315/111.51 |
| 6,113,851 A * | 9/2000 | Soloshenko et al. | 422/22 |
| 6,424,091 B1 * | 7/2002 | Sawada et al. | 315/111.81 |
| 7,192,553 B2 * | 3/2007 | Crowe et al. | 422/23 |

(Continued)

FOREIGN PATENT DOCUMENTS

WO    WO 2006/096716 A3 *    9/2006

OTHER PUBLICATIONS

Sterilization effects of atmospheric cold lasma brush, Q. S. Yu, C. Huang, F.-H. Hsieh, H. Huff, and Yixiang Duan Appl. Phys. Lett. 88, 013903 (Jan. 5, 2006); doi: 10.1063/1.2161807.*

(Continued)

*Primary Examiner* — Heidi M Eide
*Assistant Examiner* — Matthew P Saunders
(74) *Attorney, Agent, or Firm* — McBee Moore Woodward & Vanik IP, LLC (57) ABSTRACT

The provision of dental restorations can be improved by generating a cold atmospheric plasma inside the mouth of the patient and then applying that cold atmospheric plasma onto a dental restoration site. The dental restoration site can be composed of either or both of dentin and enamel. Further, the provision of dental restorations can also be improved by introducing a dental adhesive onto a dental restoration site and treating it with a cold atmospheric plasma.

19 Claims, 6 Drawing Sheets

(56) References Cited

U.S. PATENT DOCUMENTS

| | | | |
|---|---|---|---|
| 7,331,789 B2 | 2/2008 | Karmaker et al. | |
| 7,719,200 B2 | 5/2010 | Laroussi | |
| 2003/0186197 A1* | 10/2003 | Allred et al. | 433/226 |
| 2004/0202985 A1* | 10/2004 | Karmaker et al. | 433/220 |
| 2006/0028145 A1* | 2/2006 | Mohamed et al. | 315/111.21 |
| 2006/0189976 A1* | 8/2006 | Karni et al. | 606/41 |
| 2006/0096716 A1* | 9/2006 | Laroussi et al. | 315/111.21 |
| 2007/0113867 A1* | 5/2007 | Duan et al. | 134/1.1 |
| 2007/0116891 A1* | 5/2007 | Duan et al. | 427/569 |
| 2008/0064012 A1* | 3/2008 | Clark | 433/226 |
| 2008/0108015 A1* | 5/2008 | Karmaker et al. | 433/202.1 |
| 2009/0012589 A1* | 1/2009 | Watson | 607/99 |
| 2009/0142514 A1* | 6/2009 | O'Neill et al. | 427/595 |

OTHER PUBLICATIONS

Sladek et al. (Treatment of *Streptococcus mutans* biofilms with non-thermal atmospheric plasma, Letters in applied microbiology 45, (2007) pp. 318-323.*

Yixiang Duan et al.; Low-Temperature Direct Current Glow Discharges at Atmospheric Pressure; IEEE Transactions on Plasma Science; Apr. 2005; pp. 328-329; vol. 33, No. 2; 0093-3813/$20.00 @ 2005 IEEE.

Jeffrey W. Stansbury et al.; Conversion-Dependent Shrinkage Stress and Strain in Dental Resins and Composites; Dental Materials (2005) 21; pp. 56-67; Elsevier Ltd.

Jack L. Ferracane; Developing a More Complete Understanding of Stresses Produced in Dental Composites During Polymerization; Dental Materials (2005) 21; pp. 36-42; Elsevier Ltd.

John R. Condon et al.; Reduced Polymerization Stress Through Non-Bonded Nanofiller Particles; Biomaterials (2002) 23; pp. 3807-3815; Elsevier Ltd.

Roberto R. Braga et al.; Factors Involved in the Development of Polymerizaton Shrinkage Stress in Resin-Composites: A Systematic Review; Dental Materials (2005) 21; pp. 962-970; Elsevier Ltd.

Roberto R. Braga et al.; Polymerization Contraction Stress in Dual-Cure Cements and Its Effect on Interfacial Integrity of Bonded Inlays; Journal of Dentistry (2002) 30; pp. 333-340; Elsevier Ltd.

Roberto R. Braga et al.; Polymerization Contraction Stress of Low-Shrinkage Composites and Its Correlation with Microleakage with Class V Restorations; Journal of Dentistry (2004) 32; pp. 407-412; Elsevier Ltd.

Jack L. Ferracane et al.; Relationship Between Composite Contraction Stress and Leakage in Class V Cavities; Am. J. of Dentisty, vol. 16, No. 4, Aug. 2003; pp. 239-243; Oregon Health & Science University, Portland, Oregon, 97239, USA.

K.K. Choi, J.R. Condon, J.L. Ferrcane; The Effects of Adhesive Thickness on Polymerization Contraction Stress of Composite; J. Dent. Res 79(3): 812-817, 2000; Oregon Health Sciences University, Portland, Oregon, 97201, USA (contact Ferracane).

R.L. Bowen, DDS; Adhesive Bonding of Various Materials to Hard Tooth Tissues, VI. Forces Developing in Direct-Filling Materials During Hardening; JADA, vol. 74, Feb. 1967, pp. 439-445.

Hashimoto et al.; In Vivo Degradation of Resin-Dentin Bonds in Humans over 1 to 3 Years; J Dent Res 79(6) 2000; pp. 1385-1391; Hokkaido University, Hokkaido, Japan.

Michael F. Burrow et al.; Dentin Bond Durability After Three Years Using a Dentin Bonding Agent with and without Priming; Dental Materials 12:302-307, Sep. 1996; University of Melbourne, Melbourne, Australia.

L.E. Tam and R.M. Pilliar; Fracture Surface Characterization of Dentin-Bonded Interfacial Fracture Toughness Specimens; J Dent Res 73(3): 607-619, Mar. 1994; Dept. Rest. Dent., Center for Biomat, Toronto, Ontario, Canada.

Ivar A. Mjör and Vibeke Qvist; Marginal Failures of Amalgam and Composite Restorations; J Dentistry, vol. 25, No. 1, 1997; pp. 25-30; Elsevier Science Ltd., Great Britain; 0300-5712/97 $17.00+0.00.

Amaral et al; Restorative Dentistry: Influence of Resin Composite Polymerizaiton Techniques on Microleakage and Microhardness; Quintessence Int, vol. 33, No. 9, Oct. 2002; pp. 685-689.

Martin Brännström; Buonocore Memorial Lecture: Communication Between the Oral Cavity and the Dental Pulp Associated with Restorative Treatment; Operative Dentistry, 1984, vol. 9, pp. 57-68; Huddinge, Sweden.

J. Robert Kelly; Ceramics in Restorative and Prosthetic Dentistry; Annual Reviews Inc. Nat. Inst. Standards and Tech, Gaithersburg, Maryland 20899 USA; Annu.Rev.Mater.Sci., 1997, 27:443-468.

Thomas J. Hilton; Can Modern Restorative Procedures and Materials Reliably Seal Cavities? In Vitro Investigations. Part 1; Am J Dent, vol. 15, No. 3, Jun. 2002, pp. 198-210.

K-H Friedl et al., Placement and Replacement of Composite Retorations in Germany; Operatiave Dentistry, 1995, vol. 20, pp. 34-38, University of Regensburg, Regensburg, Germany.

Nairn H. F. Wilson et al., Reasons for Placement and Replacement of Restorations of Direct Restorative Materials by a Selected Group of Practicioners in the United Kingdom; Quintessence Int, vol. 28, No. 4, Apr. 1997, pp. 245-248.

C. L. Davidson et al., The Composite between the Composite-Dentin Bond Strength and the Polymerization Contraction Stress; J. Dent. Res.; vol. 63, No. 12, Dec. 1984, pp. 1396-1399; Dept. of , U. of Amsterdam, Amsterdam, Netherlands.

M. Hanning et al., Comparative In Vivo and In Vitro Investigation of Interfacial Bond Variability; Operative Dent, Jan. 2001, vol. 26, No. 1, pp. 3-11, U. of Missouri-KC, USA, (ISSN 0361-7734).

Hilde Tobi et al.; Cost-effectiveness of Composite Resins and Amalgam Class II Restorations; Community Dent Oral Epidemiol; Apr. 28, 1999; vol. 27, pp. 137-143; ACTA, Amsterdam, Netherlands; (ISSN 0301-5661).

Yong Wang et al.; Interfacial Chemistry of Class II Composite Restoration: Structure Analysis; J. Biom Mat Res—Part A; Dec. 1, 2005, vol. 75A, No. 3, pp. 580-587; Wiley Publications: ISSN 1549-3296.

Hakon Nordbo et al.; Saucer-shaped Cavity Preparations for Posterior Approximal Resin Composite Restorations: Observations up to 10 years; Quintessence Int, Jan. 1998, vol. 29, No. 1, pp. 5-11; U. of Missouri-KC, USA.

Hakon Nordbo et al.; Saucer-shaped Cavity Preparation for Composite Resin Restorations in Class II Carious Lesions: Three-year Results; J Pros Dent, Feb. 1993, vol. 69, No. 2, pp. 155-159; Mosby-Year Book, St. Louis MO, USA (ISSN 0022-3913).

H. Letzel; Survival Rates and Reasons for Failure of Posterior Composite Restorations in Multicentre Clinical Trial; J. Dent, 1989, vol. 17, pp. S10-S17; Butterworth & Co.: 0300-5712/89/S10S10-08.

C. J. Collins et al.; A Clinical Evaluation of Posterior Composite Resin Restorations: 8-Year Findings; J. Dent; 1998; vol. 26; No. 4; pp. 311-317; Elsevier Science, Great Britain, 0300-5712/98.

Felix U. Lutz, et al.; Advanced Adhesive Restorations: The Post-Amalgam Age; PP&A; May 1996; vol. 8, No. 4; pp. 385-394; Zurich, Switzerland.

Helena Forss et al.; From Amalgam to Composite: Selection of Restorative Materials and Restoration Longevity in Finlind; ACTA Odontologica Scan, Apr. 2001; vol. 59, No. 2, Kuopio U. Hospital, Kuopio, Finland (ISSN 0001-6357).

Ivar A. Mjor; The Reasons for Replacement and the Age of Failed Restorations in General Dental Practice; ACTA Odontol Scan; Jan. 1997; vol. 55, No. 1; pp. 58-63; Oslo, Norway; ISSN 0001-6357.

A. K. York et al.; Reasons for Placement and Replacement of Dental Restorations in the United States Navy Dental Corps; Operative Dent; 1993; vol. 18, No. 5; pp. 169-216; ISSN 0361-7734.

David C. Sarrett; Clinical Challenges and the Relevance of Materials Testing for Posterior Composite Restorations; Dent Materials; Jan. 2005; vol. 21, No. 1, pp. 9-20; ISSN 0109-5641.

L. E. Tam et al.; Effects of Dentin Surface Treatments on the Fracture Toughness and Tensile Bond Strength of a Dentin-Composite Adhesive Interface; J Dent Res; Sep. 1994; vol. 73, No. 9; pp. 1530-1538; Toronto, Ontario, Canada.

A. John Gwinnett; Quantitative Contribution of Resin Infiltration/Hybridization to Dentin Bonding; Am J Dent; Feb. 1993, vol. 6, No. 1, pp. 7-9; New York, USA.

(56) References Cited

OTHER PUBLICATIONS

David H. Pashley et al.; Permeability of Dentin to Adhesive Agents; Adhesives Symposium; Quintessence Int; Sep. 1993; vol. 24, No. 9; pp. 618-631.

Grayson W. Marshall, Jr.; Dentin: Microstructure and Characterization; Adhesives Symposium; Quintessence Int; Sep. 1993; vol. 24, No. 9; pp. 606-617.

Y. Wang et al.; Hybridization Efficiency of the Adhesive/Dentin Interface with Wet Bonding; J Dent Res; Feb. 2003, vol. 82, No. 2; pp. 141-145.

J. D. Eick et al.; Current Concepts on Adhesion to Dentin; Crit Rev Oral Biol Med; Aug. 1997; vol. 8, Issue 3; pp. 306-335.

B. Van Meerbeek et al.; Morphological Aspects of the Resin-Dentin Interdiffusion Zone with Different Dentin Adhesive Systems; J Dent Res; Aug. 1992; vol. 71, No. 8; pp. 1530-1540; Washington, D.C., USA.

A. Banerjee et al.; Dentine Caries Excavation: A Review of Current Clinical Tehniques; British Dent J; May 2000; vol. 188, No. 9; pp. 476-482; www.bdj.co.uk.

H. K. Yip et al.; Caries Removal Techniques and Instrumentation: A Review; Clin Oral Invest; Dec. 1998, vol. 2, No. 4; pp. 148-154; © Springer-Verlag 1984.

Jan W.V. Van Dijken et al.; Long-Term Dentin Retention of Etch-and-Rinse and Self-Etch Adhesives and a Resin-Modified Glass Ionomer Cement in Non-Carious Cervical Lesions; Dental Materials, Jul. 2008, vol. 24, No. 7; pp. 915-922; www.sciencedirect.com.

Ralph W. Phillips; Advancements in Adhesive Restorative Dental Materials; J Dent Research; Nov.-Dec. 1966; vol. 45, No. 6, Part 1; pp. 1662-1667; The American Dental Association.

Masanori Hashimoto et al.; Fractographical Analysis of REsin-Dentin Bonds; Am J Dent; Dec. 2001; vol. 14, No. 6; pp. 355-360; Ishikari-Tobetsu, Japan; e-mail: masanori-h@mue.biglobe.ne.jp.

Edward J. Swift, Jr.; Dentin Bonding; Ask the Experts; vol. 15, No. 2; 2003; p. 71.

Q. S. Yu, et al.; Sterilization Effects of Atmospheric Cold Plasma Brush; Applied Physics Letters; 88; 013903-1; 2006 Am Inst of Physics; (0003-695/2006/88(1)/013903/3/$23.00.

Qingsong Yu; Dentin Surface Treament by Atmoshperic Plasma Brush for Enhanced Adhesive/Dentin Interfacial Bonding; 1 Center for Surface Sci & Plasma Tech, 2 Dept. Oral Biology, U of Missouri Columbia; Fax: 573 884 4940; E-mail: yuq@missouri.edu.

* cited by examiner

ATMOSPHERIC NON-THERMAL GAS PLASMA METHOD FOR DENTAL SURFACE TREATMENT

CROSS-REFERENCE TO RELATED APPLICATIONS

This application claims the benefit of U.S. Provisional Application No. 61/214,450 entitled "Atmospheric Non-Thermal Gas Plasma Method for Dental Surface Treatment" filed Apr. 23, 2009 by Qingsong Yu, Hao Li, and Meng Chen.

GRANT STATEMENT

This invention was made with government support under contract No. NSF CBET-0730505 awarded by the National Science Foundation. The government has certain rights in the invention.

BACKGROUND OF THE INVENTION

The present disclosure relates to dental cavity repair and treatment. More specifically, the present disclosure relates to a surface treatment method for targeted dentin and dental materials using a cold atmospheric discharge plasma technique to improve the clinical performance and durability of dental restorations.

Dental fillings are commonly used to treat dental cavities resulting from caries. Caries is the formal name for the disease that causes tooth decay or the formation of what are commonly referred to as cavities. Caries causes tooth decay resulting in decayed matter forming in the tooth, the location of the decayed matter often being referred to as a cavity. As many know, the tooth has an enamel outer layer that covers a thicker layer of dentin. The enamel protects the dentin, and in turn, the dentin protects the pulp of the tooth that contains flesh, including sensitive nerves. Failure of the enamel and the dentin to protect the pulp, whether from accident or caries, is a toothache.

To treat caries, the decayed matter in the cavities needs be removed and the cavities are disinfected and filled. The removal of the decayed matter is usually performed by a dental drill. The materials for the filling are most commonly dental amalgam or composite material. Conventionally, an adhesive is used to firmly connect the tooth to the filling. Adhesives are also used for crowns and caps. A generic term that encompasses fillings, crowns, caps and other structures installed in a tooth to remedy a defect in the tooth is restorations.

Also, one restoration is being replaced with another restoration can be performed. Such replacement is sometimes, but not always, accompanied by the presence of additional decay that needs removal. The prior restoration will usually be removed in the course of this work, sometimes by drilling, but also by other means in situations such as where a crown or a cap is being removed.

The tooth may be formed to have a recess in the tooth, as is common for dental fillings. But the tooth may also be formed into a post or the like, such as when caps are installed.

Where the surfaces of the tooth, adhesive and filling meet each other are called interfaces. For a properly installed filling there is an interface between tooth and adhesive and an interface between adhesive and filling. Fillings have high failure rates at these interfaces and often need to be replaced later.

Failure is particularly prominent in composite dental materials. Composite restoration has become the preferred form of restorative material because of patients' aesthetic requirements and the aversion of patients and dentists to the potential health risk of mercury release from dental amalgams. But composite restorations do not last as long as dental amalgams. Some of the reasons for premature failures of composite restoration include dental composite shrinkage, inadequate bonding of the adhesive to dentin, and formation of a second cavity at the edges of or under the restoration.

Recent studies show that many recorded filling failures occur at the tooth-adhesive interface. These failures are caused by the failure of the adhesive bonding attaching the filling material/composite to the dentin of the tooth. One study has reported that about 70% of composite restoration failures at the back of the mouth occur at the dentin-composite interface. The failure of the adhesive to maintain bonding results in the separation of the composite restoration from dentin. The resulting gaps lead to staining at the margins of the restoration, sensitivity, and recurrent caries, which cause a significant portion of composite restoration removal and replacements.

Studies also show that adhesion between enamel and composite is generally adequate for clinical applications, while adhesive/dentin bonds are the weak link and the interfacial bond strength in the composite restoration deteriorates significantly over time. The disruption of the bonded interface can develop as a consequence of long-term thermal and mechanical stresses, or during the restorative procedure itself, due to stresses generated by composite polymer shrinkage.

Foods and saliva are perpetually in the mouth, and further, bacteria are always present. These can cause problems for the adhesive working to maintain bonding at the restoration-dentin interface. Unsuccessful dentin bonding also means that there are sites at the tooth restoration interface that are vulnerable to hydrolytic breakdown and susceptible to attack by bacterial enzymes. Clinical performance needs to improve when polymer-based dental composites are to be considered viable alternative to dental amalgam. The desired improvements include enhancing the bonding strength at the adhesive/dentin interface to resist polymerization shrinkage and to make it impervious to oral fluids.

Currently, the preparation and disinfection of dental cavities (dentin surfaces) prior to filling relies on mechanical drilling or laser techniques to remove dead (synonymous with necrotic), infected, and non-remineralizable tissue. Both methods are often destructive and can be painful for patients due to mechanical stimulation (vibration) and heating of the dental nerve. To ensure sufficient disinfection, an excess healthy tissue must be removed using the current methods, since dentine contains many small channels in which bacteria can hide. Moreover, the disinfection process itself, with the current methods, can also lead to fracture of dentin.

Several studies and techniques for the preparation/disinfection process have been attempted to improve the interface bonding strength, but with only limited success. For example, U.S. Pat. No. 6,172,130 describes surface treatment of dental prosthesis composed of polymers containing hydrogen atoms using gas phase plasma in a vacuumed reactor vessel operated at 13.56 MHz. The plasma treated polymers are characterized by the hydrogen atoms on the surface of the polymer being partially replaced by fluorine atoms. The type of modified polymers is claimed to be able to improve the retention of the prosthesis and/or limit the development of dental plaque. However, this plasma process, due to its requirement of reduced-pressure environment, is not suitable for surface treatment of the dentin of living subjects in dental clinics.

Therefore, there is a need to develop a new and improved preparation/disinfection method employing the cold atmospheric plasma technology, which can chemically activate dentin surface to implement chemical bonding and enhance adhesion strength at dentin-composite interfaces, and consequently to increase the longevity of dental restorations, as well as to be more cost-effective and less painful to patients.

SUMMARY OF INVENTION

A method of surface treatment for providing a dental restoration can include generating a cold atmospheric plasma inside the mouth of the patient and then applying that cold atmospheric plasma onto a dental restoration site. The dental restoration site can be composed of either or both of dentin and enamel. Also, the surface of dental adhesive present after introducing a dental adhesive onto a tooth can also constitute a dental restoration site that can be beneficially treated with a cold atmospheric plasma.

The dental restoration can also have a surface of dental composite layers. The temperature of the cold atmospheric plasma can range from about 10° C. to about 50° C. with temperatures of about 35° C. to about 39° C. being preferred for patient comfort in most applications. The gas that is excited into the cold atmospheric plasma can be helium, argon, nitrogen, oxygen, nitrous oxide, ammonia, carbon dioxide, water vapor, air, gaseous hydrocarbons, gaseous silicon-carbons, gaseous fluorocarbons or mixtures thereof.

Also, the atmospheric plasma can be applied to the restoration site for a period of about 10 seconds to a period of about 2 minutes. In addition to measuring exposure by a fixed time interval, the method contemplates the atmospheric plasma being applied to the restoration site for a period of time that enhances the strength of the adhesive-site interface.

The cold atmospheric plasma appears to be most beneficial to the periphery of a dental restoration site.

This disclosure also contemplates a method of installing a dental restoration on a tooth inside of a patient's mouth where material is removed from a tooth to expose a surface comprising dentin or enamel. The exposed surface is then treated with a dentally acceptable acid to clean it, and then the acid is removed to stop the acid-tooth reaction. Then cold atmospheric plasma is generated inside the mouth of the patient and applied onto the exposed surface. Then a dental adhesive is applied to the surface. Optionally the cold atmospheric plasma can be applied to the adhesive-coated surface. Then a dental restoration can be installed on the adhesive coated surface.

DETAILED DESCRIPTION OF THE INVENTION

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The present disclosure reveals a new and improved surface treatment method using cold atmospheric plasma brush technology that can be used in dental restoration for dental cavity treatment, preparation, and surface modification of related dental fillings. The disclosed treatments can be safely used inside the mouth of a patient without causing more pain than is common to standard dental work. The surface treatment method can be employed in any surface to activate chemical bonding effect, particularly the surfaces of a dental filling site in a dental restoration, such as dentin surface, dental enamel surface, dental-adhesive surface, and dental-filling surface. The method for surface treatment at a dental restoration site during a dental restoration can include generating cold atmospheric plasma at an appropriate temperature and directing the plasma jet onto a desired surface at the dental restoration site for duration sufficient to change the surface characteristics in ways that facilitate bonding of the treated site with adhesives.

Cold plasmas, or low-temperature gas plasmas, are partially ionized gases that contain highly reactive particles including electronically excited atoms, molecules, ionic and free radical species, while the gas phase remains near room temperature. Depending on the plasma chemistry or gas composition, these highly reactive plasma species clean, and etch surface materials, bond to various substrates, or combine to form a nanoscale thin layer of plasma coating, and consequently alter the surface characteristics. These non-equilibrium plasmas combine exceptional chemical activity with relatively mild, non-destructive characteristics due to the room-temperature gas phase.

The cold atmospheric plasma can comprise plasma gases of helium, argon, nitrogen, oxygen, nitrous oxide, ammonia, carbon dioxide, water vapor, air, gaseous hydrocarbons, gaseous fluorocarbons, gaseous silicon-carbons, and mixtures of them. Desirably, the temperature of the plasma can range from about 20 to about 50° C., with about 37±2° C. as preferred. The surface of the desired dental filling site can be the surface of a dentin, the surface of dental enamel, the surface of a dental adhesive, or the surface of a dental filling.

The term, "adhesive" or "dental adhesive" refers to a composition used on a dental structure (e.g., a tooth) to adhere a restoration material to it. Non-limiting examples of such products are listed in Table 1.

TABLE 1

| Company Name | Bonding Products |
|---|---|
| 3M/ESPE | Prompt L-Pop, Prompt SE, Scotchbond SE, Scotchbond Multipurpose Plus, Scotchbond Multipurpose, Easy Bond SE, Single Bond Plus |
| ALL DENTAL PRODUCTS | ComposiRepair |
| BISCO | Elitebond, All-Bond 2, All-Bond 3, All-Bond SE, One Step, One Step Plus, Tyrian SPE |
| CENTRIX | Multibond, Adhere |
| COLTENE WHALEDENT | One Coat Bond, One Coat 7.0, One Coat SE, Coltene ART Bond |
| COOLEY & COOLEY | Snapbond |
| COSMEDENT | Powerbond, Complete |
| DE TREY/DENTSPLY | PRIME & BOND NT, Xeno III, Xeno IV, XP Bond, ProBond |
| DENMAT | Tenure Bond, Tenure S, Tenure Uni-Bond, Tenure A&B, Tenure Quick |
| DISCUS DENTAL | Cabrio |
| GC AMERICA | Fuji Bond LC, Unifil Bond LC |
| HENRY SCHEIN | Dentin Bonding Agent, Natural Elegance Prime Bond, Sun Schein Bond |
| HERAEUS KULZER | Gluma Solid Bond, Denthesive II, Gluma Comfort Bond, Gluma One Bond, Gluma Gold Bond, i Bond, i Bond SE |
| IVOCLAR/VIVADENT | ExciTE, Heliobond, Syntac Sprint, Syntac Single Component, Syntac 3, AdheSE |
| J. MORITA | One up Bond F, M-Bond |
| KERR | XR-Bond, Optibond, Optibond FL, Optibond Solo, Optibond Solo Plus, Self Etching, Optibond All in One |
| KURARAY | Clearfil liner bond 2, Clearfil liner bond 2V, Clearfil DC Bond, Clearfil SE bond, Clearfil Photobond, S3 Bond, New Bond |
| L.D. CAULK/ DENTSPLY | Prime & Bond NR, Probond, Xeno III, Xeno IV, XP Bond |
| PARKELL | Touch & Bond, Easy Bond, C&B Metabond, Totalbond, Brush & Bond, Etch Free |
| PENTRON CLINICAL TECHNOLOGIES | Bond 1, Nano Bond, Bond 1 SF Solvent Free SE, Bond It, Bond 1 C&B |
| PREMIER | Integrabond, Bond Boost SE |
| PULPDENT | Dentastic Uno, Dentastic Uno Duo, Dentastic |
| SHOFU | Imperva Bond, Beautibond, Fl Bond |
| TOKUYAMA | Mac-bond II, Bond Force |
| ULTRADENT | Permaquik, Permagen, PQ1 |
| VOCO | Solobond M, Admira Bond |

Cold plasma surface treatments, when employed to modify the surface of the dentine, can increase adhesive penetration into collagen fibrils leading to a more effective hybrid layer and increasing chemical bonding between the collage fibrils and the dental adhesive. The plasma can also act as a primer for the collagen fibers. Low temperature plasmas in particular, when modifying polymers for adhesion, can be tailored to reduce the negative effects seen with other preparatory methods such as surface roughening, wet chemical treatments, or exposure to flames.

Dentin is largely a matrix of hydroxyapatite having fibrils of collagen distributed within the hydroxyapatite. While not wishing to be bound by theory, it is believed that when utilized correctly and efficiently cold plasma is a gentle method used to increase the wettability of the topmost layer of polymeric surfaces, such as collagen fibrils, without negatively affecting the underlying material. Plasma can also uniquely tailor the surface of polymeric materials by addition of reactive gases in small quantities, which permits the plasma to easily modify and enhance the surface characteristics of various types of adhesives. Additionally, cold atmospheric plasma is a good candidate to sterilize the surface of surgical instrumentation to prevent bacterial infection, which in turn decreases the chance of the composite failing because of the formation of secondary caries.

The inventive surface treatment method for a dental filling site includes the steps of 1) generating cold atmospheric plasma at a pre-determined temperature, and 2) directing the plasma onto a desired surface at the dental filling site for duration sufficient to change the surface characteristics.

Figure 1:
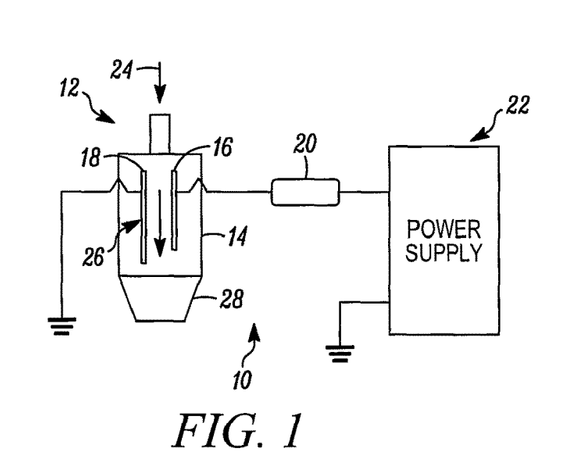
FIG. 1 is a schematic of the apparatus to generate a cold atmospheric plasma.

FIG. 1, is a schematic illustration of a typical dental plasma brush and related power supply. The plasma brush device 10 contains a plasma brush generator 12 that includes a walled, narrow gas chamber 14 and two electrodes 16 & 18, which are located inside the gas chamber 14. The hot wire electrode 16 is connected to an optional ballasted resistor 20 that can be used to restrain the discharge current coming from the external power source 22. The grounded electrode 18 is connected to ground.

A working gas 24 can be introduced into the gas chamber 14. When electrical power is applied through the electrodes 16 & 18, the gas in the gas chamber 14 is excited. A glow discharge plasma 26 of the gas flowing through the plasma generator will be formed. The discharge plasma 26 will exit through a nozzle 28, which can be disposable for control of hygiene.

The electrodes can be powered by an external power source 22. The atmospheric pressure plasma can be generated and maintained by electric power input from a direct current or alternating current, audio or radio frequency, or pulsed power supplies. The working gas 24 can be helium, argon, nitrogen, oxygen, nitrous oxide, ammonia, carbon dioxide, water vapor, air, gaseous hydrocarbons, gaseous fluorocarbons, gaseous silicon-carbons, and mixtures thereof. Argon or air is preferred in certain dental applications, such as enhancement of bonding strength in dental restoration, or disinfection of dental bacteria. The duration of each surface treatment varies depending upon the particular application, but commonly run less than 60 seconds.

A nozzle 28 is used to direct the flow of the discharge plasma out of the gas chamber 14. The nozzle 28 can be in any shape. For example, the exit from the nozzle 28 can be round, oval or square, or other desirable shape. Additionally, it is desirable for the shape of the gas chamber 14 to complement the shape of the nozzle 28.

One operable shape is a nozzle 28 that is relatively narrow in a first direction generally perpendicular to the flow of gas and relatively wide in a second direction transverse to the first direction but still generally perpendicular to the flow of gas. Such a nozzle 28 forms plasma with a brush-like shape at the exit of the chamber. Operatively, when the nozzle 28 forms a brush of plasma, the gas chamber 14 is dimensioned slit-like to complement the nozzle 28.

While the plasma brush would be operable without a ballasted resistor 20, glow-to-arc transitions can be prevented by a ballasted resistor 20 and working gas 24 appropriate to the narrow slit chamber design. The brush-like shaped plasma extends beyond the exit of the chamber, and possesses there active features of low-pressure or non-equilibrium plasmas. The resultant low-pressure or non-equilibrium gasses can be used to treat surfaces of dentin, enamel, adhesive, or dental composite layer for dental composite filling.

Further information on the plasma brush are incorporated by reference as if fully set forth herein from Y. X. Duan, C. Huang, Q. S. Yu, 2005, "Low-temperature direct current glow discharges at atmospheric pressure", *IEEE Transactions on Plasma Science*, 33, p. 328-329.

Figure 2A:
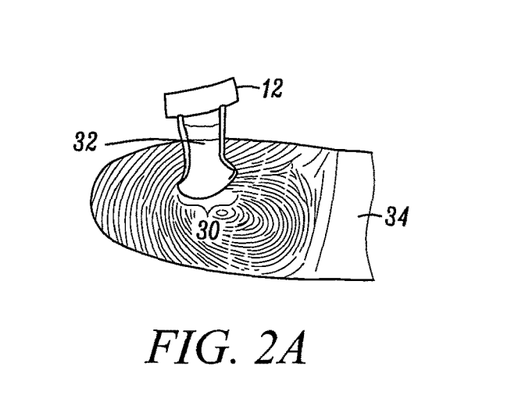
FIG. 2(a) is a drawing of the cold atmospheric plasma source suitable for dental applications, according to one embodiment of the invention.
Figure 2B:
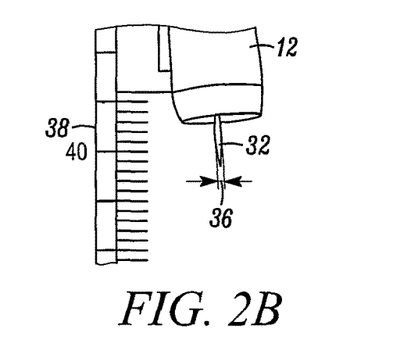
FIG. 2(b) is a drawing of the cold atmospheric plasma source suitable for dental applications; according to one embodiment of the invention.

The plasma can be directed to the surface of dentin, enamel, dental adhesives, or dental fillings. FIG. 2(*a*) is a side view facing a broad aspect 30 of the plasma brush 32. The width of the plasma brush is desirably in the range of 1 to 10 mm. The diagram shows the plasma to be safe to apply to a human finger 34, which can be readily done. FIG. 2(*b*) shows a side view facing the narrow aspect 36 of the plasma "brush." The narrow aspect 36 of the plasma brush 32 has a thickness of about 1-5 mm, and is desirable in the range of 1 to 3 mm. A ruler 38 is also shown indicating a length 40 for the plasma brush 32 of about 5 mm, and is desirable in the range of 5 to 12 mm.

When employing the atmospheric plasma brush, the size and temperature of the plasma can be easily controlled by varying the plasma input power mainly through adjusting the electrical current to the electrodes and gas flow rate passing the plasma chamber. The desired temperature of the plasma ranges from about 20 to about 50° C. A plasma temperature of about 37±2° C. is preferred for work in humans. It should be noted that the temperature can be adjusted to suit the comfort of a particular patient or other species of animal.

Figure 3:
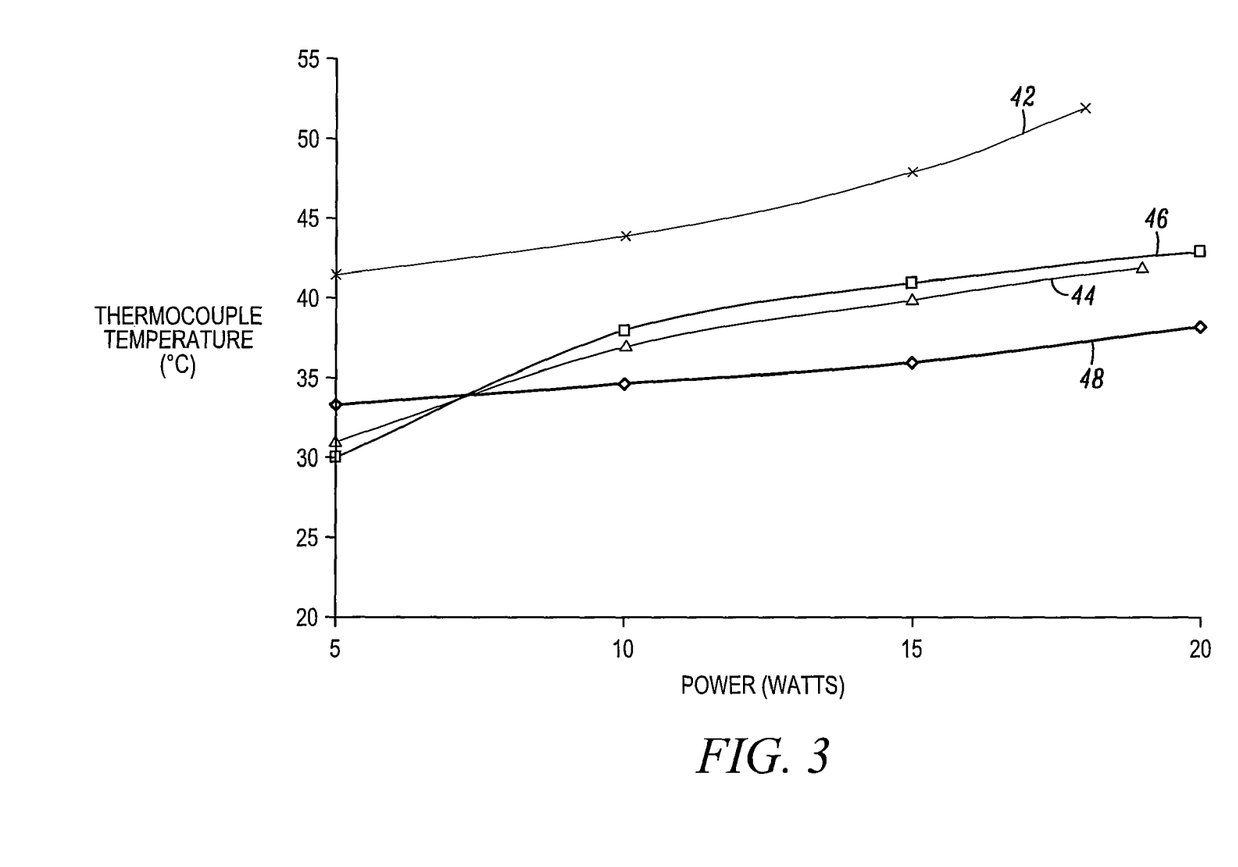
FIG. 3 shows the various plasma temperatures at different plasma operating conditions, including power input and argon flow rate.

FIG. 3 is a graph showing various plasma temperatures under different generating conditions. Line 42 denotes the thermocouple temperature (Y-axis) as a function of power source wattage at a constant flow of argon gas at 2000 standard cubic centimeters per minute (sccm). Line 44 shows the same at a flow rate of 3000 sccm, line 46 at 4000 sccm, and line 48 at 5000 sccm. Thermocouple, IR imaging, and thermometers, when used in correlation, can be used to provide a reasonable range of the plasma temperatures.

The plasma temperature profile of the described atmospheric plasma brush was established by taking thermal IR images. In comparison with the plasma temperatures measured using a thermocouple, it was noted that an average of 5° C. higher temperature was recorded using the IR imaging method. The nerve system of human teeth is very sensitive to temperature differences. The results of the thermal imaging study indicate that the plasma temperature of the plasma brush can be well controlled to be close to human body temperature.

The duration of treatment can vary from 5 seconds to 10 minutes. The preferred treatment time will be in the range of 10 seconds to 2 minutes and the most preferred range will be in the range of 10 seconds to 60 seconds.

In a particular application, dentin surfaces were treated by argon plasma brush at room temperature for 0, 30, 100, and 300 sec. Adper Single Bond Plus dental adhesive (3M ESPE) and Filtek Z250 composite (3M ESPE) were applied and light cured as directed.

Figure 4:
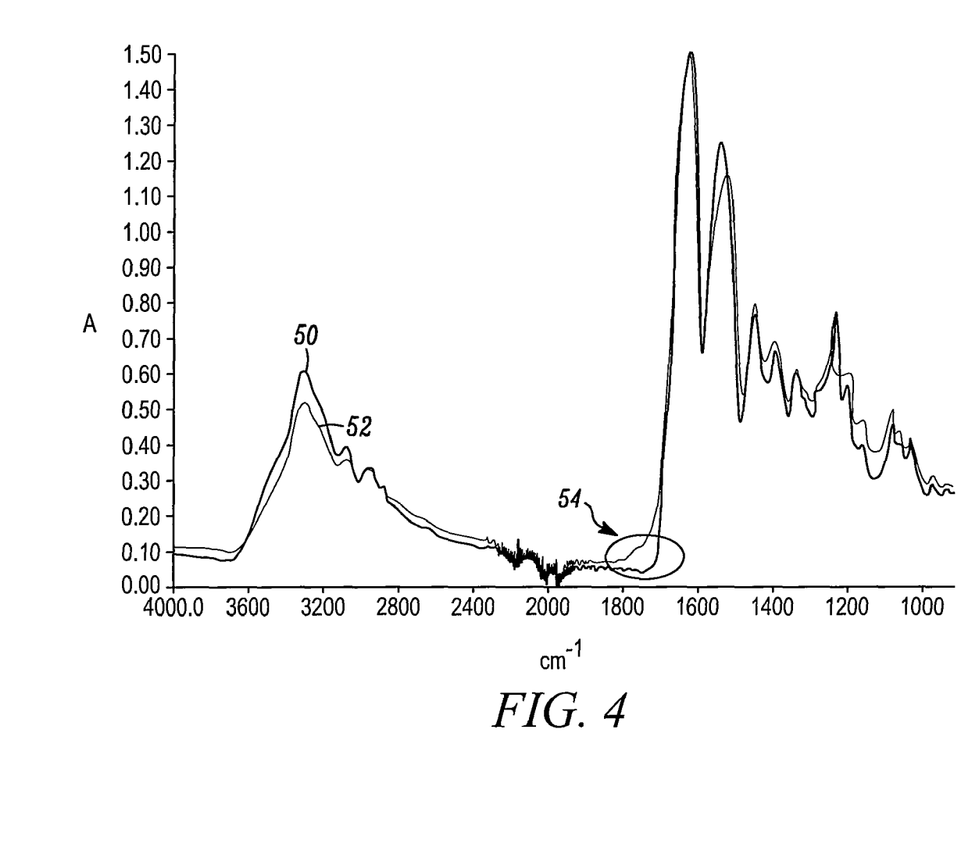
FIG. 4 shows the Fourier Transform Infrared (FTIR) spectrum change of dentin at surface before and after plasma treatment.

FIG. 4 shows the Fourier Transform Infrared (FTIR) spectrum change of dentin surface before plasma treatment 50 and after plasma treatment 52. The FTIR spectrum change after plasma treatment shows that there is a significant chemical change on the dentin surface. One change is the increase of carbonyl groups present at the surface, shown in area 54, which can contribute, in part, to the enhancement of the bonding strength at dentin-composite interfaces. While not wishing to be bound by theory, the formation of more carbonyl groups on the collagen fibers can increase hydrogen bonding between adhesive and fiber. These additional functional groups also can permit the collagen fibers to disaggregate after rewetting because of the electrical repulsive forces, which can significantly increase the surface area of the collagen fibers and in turn the bonding strength of the collagen fibers to adhesives.

This can be understood in view of the composition of representative collagens and adhesives. Type I collagen is one type of collagen present in dentin. Type I collagen is generally about ⅓ glycine and ⅙ proline or hydroxyproline. Lysine, hydroxylysine, and histidine are generally involved in cross-linking type I collagen molecules into fibrils. ADPER SINGLE BOND PLUS is a representative dental adhesive. ADPER SINGLE BOND PLUS comprises Bis-GMA, dimethacrylates, HEMA, VITREBOND polyalkenoic acid copolymer, water, ethanol, and silica nanoparticles. All of these can have hydrogen bonding with the recited components of Type I collagen.

Dentin collagen has 3 times the hydroxylysine as skin collagen. When treated with HEMA and glutaraldehyde only 18% of the lysine and 15% of the hydroxylysine are cross-linked. Steric hindrance prevents more than 80% of the free amino acids from interacting with the adhesive. As a result, opportunities for hydrogen bonding are severely reduced in a collagen fiber as compared to the separate parts of a collagen molecule.

While not wishing to be bound by theory, the plasma is thought to disaggregate the triple helix. The result of the disaggregation can be that the amino acids that were held in the interior of the triple helix are exposed by breaking up the triple helix. Not only does this result in more amino acids being exposed, it increases the surface area exposed for adhesion by taking surface area that was on the inside of a fiber, and making that surface area available for adhesion.

The techniques of the present disclosure result in an increase in the ultimate tensile strength for the dentin-composite bond induced by plasma treatment of dentin-composite interfaces at the margins of the interfaces. The increase of carbonyl groups on plasma treated dentin surfaces shown in the FTIR implies the treatment effect is due to the reactive species in the plasma rather than the heat produced from the plasma brush. Both heat treated and plasma treated surfaces show an amide II shift. In other words, plasma treatment did induce chemical structural changes on the collagen fibrils, which determines the final interfacial bonding strength of dental composite restorations.

Figure 5:
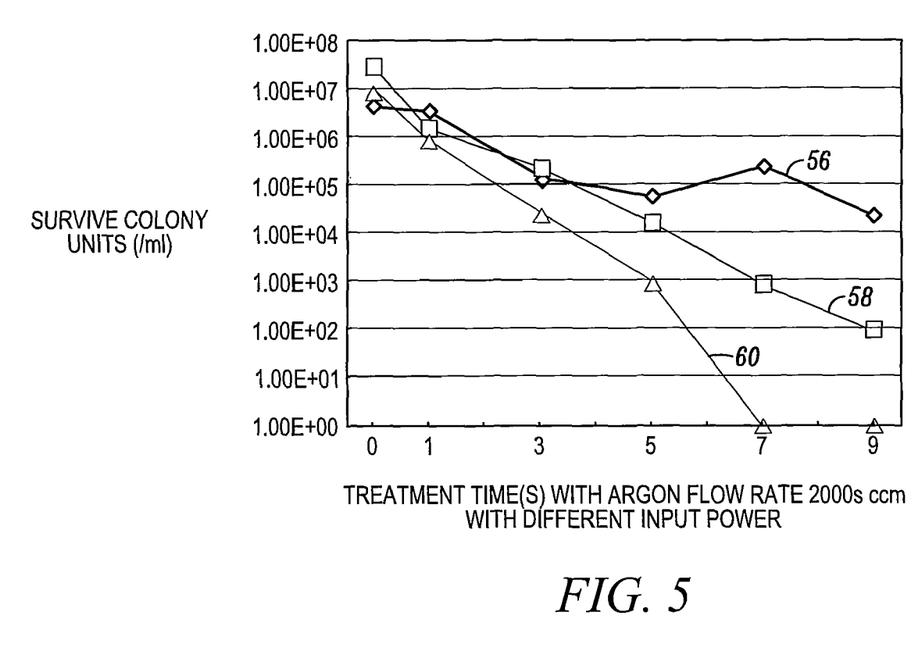
FIG. 5 shows the plasma treatment effects on cell survival curves of *Streptococcus mutans*, which is the most common bacterium causing dental cavity.

Furthermore, the plasma treatment at the dental filling site provides additional disinfection effects besides improving bonding strength. FIG. 5 shows the plasma treatment effects on cell survival curves of Streptococcus mutans, the most common bacterium causing dental cavity. The Y-axis of FIG. 5 is the Y-axis of colony-forming unit (CFU), a measure of viable bacterial numbers, and the X-axis is the treatment time with argon at a flow rate of 2000 sccm. Line 56 represents the results at 5 W of power, line 58 at 10 W of power and line 60 at 15 W of power. The results shown in FIG. 5 demonstrate that plasma treatment can also effectively and rapidly disinfect bacteria in the cavity.

EXAMPLE 1

Figure 6:
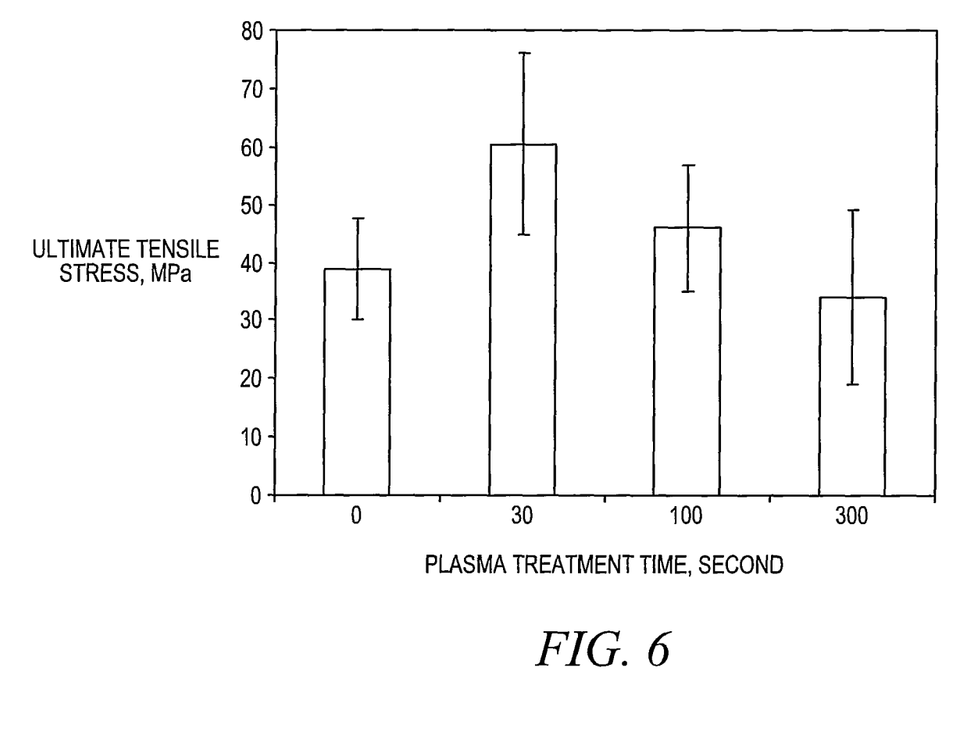
FIG. 6 illustrates the bonding strength improvement for dental composite restoration induced by plasma treatment of dentin/composite interfaces.
Figure 7:
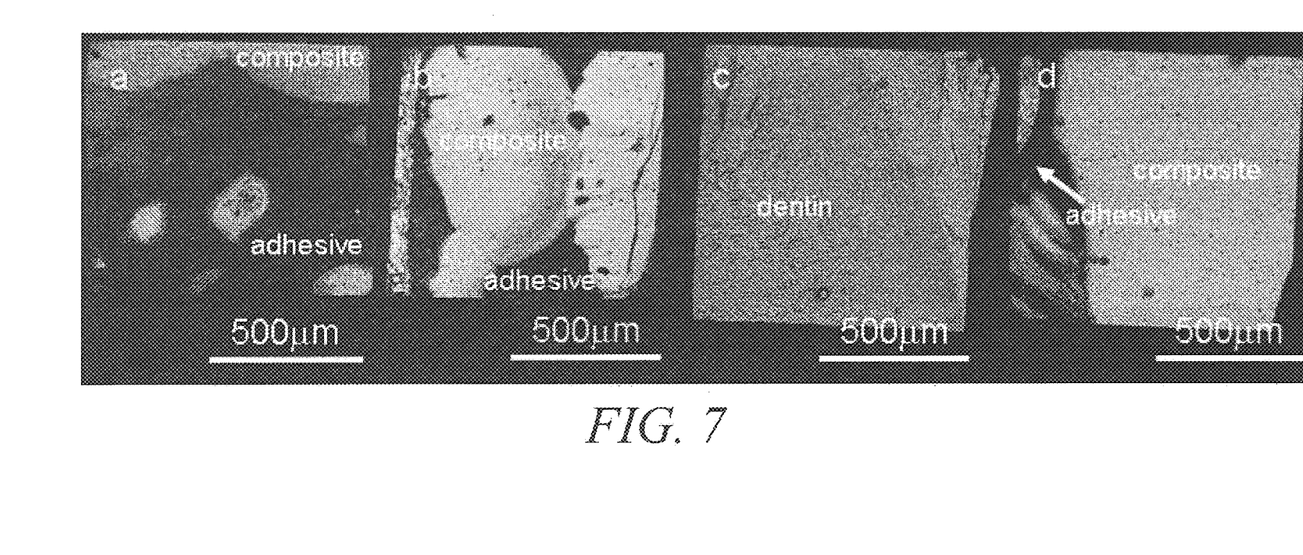
FIG. 7(a) is an scanning electron microscope (SEM) image taken of a fracture at an untreated interface.
FIG. 7(b) is an SEM image taken of a fracture at an interface generated from 30 seconds of plasma treatment.
FIG. 7(c) is an SEM image taken of a fracture at an interface generated from 100 seconds of plasma treatment.
FIG. 7(d) is an SEM image taken of a fracture at an interface generated from 300 seconds of plasma treatment.

An atmospheric cold plasma brush (ACPB), a non-thermal gas plasma source, was used to treat and prepare dentin surfaces for dental adhesive and dental composite application. Extracted unerupted human third molars were used for this investigation. The occlusal one-third of the crown was sectioned by means of a water-cooled low speed diamond saw (Buehler, Lake Bluff, Ill.). The exposed dentin surfaces were polished with 600 grit SiC sand papers under water and then etched using 36% phosphoric acid. Dentin surfaces were Ar plasma treated for 0, 30, 60, and 300 sec. A flow rate of 2500 sccm and a power of 5 watts were chosen. The results of these treatments are shown in FIG. 6. Oxygen additions at various flow rates were also tested. Adper Single Bond Plus dental adhesive (3M ESPE) and Filtek Z250 composite (3M ESPE) were applied and light cured as directed. Dentin/composite bars (8-10 mm×1 mm×1 mm) were cut from the prepared teeth for tensile testing and interface characterization. The chemical structural changes of the plasma treated dentins were characterized by FTIR. Fracture surfaces were characterized by SEM (Philips XL30 ESEM-FEG).

When plasma treatment was not used, the strength of a dentin-adhesive interface was 36.8±10.5 Mpa. But 30 seconds of plasma treatment on the dentin surface increased the tensile strength of the dentin/adhesive interface of peripheral dentin to 60.4±15.7 Mpa. These findings were confirmed with SEM. The notion of peripheral dentin is understood in the art. One definition is given by viewing the tooth from above. If the dentin is above pulp, it is central and the remaining area is peripheral. It can also be understood as being the most peripheral 1 to 2 mm or so of the tooth. The SEM observations show increased areas of composite on the fracture surface when compared to the untreated control samples. It was found that numerous plasma treated samples failed in locations other than the dentin/adhesive interface, while most of the control samples failed at the interface. The periphery is an area that in a particular planned or installed restoration is most exposed to the contents of the mouth, including, but not limited to, saliva, bacteria and food.

EXAMPLE 2

SEM images shown in FIGS. 7(a)-(d) have been taken of the fracture surfaces that can be generated using methods of this disclosure. FIGS. 7(a)-(d) represent back scattered SEM images of the fracture surfaces of the test specimens prepared from: (a) the untreated controls (0 sec), (b) 30 sec, (c) 100 sec, and (d) 300 sec plasma treated dentin. The resulting SEM images showed that more composite remained on dentin surfaces plasma treated for 30 seconds when compared with controls. This illustrates that rather than the fissure occurring in the adhesive-dentin interface, the break occurs in the composite instead, showing that the adhesion of the interface is stronger than the internal strength of the composite.

Fracture modes were determined and recorded. Table 2 presents micro tensile test data and fracture location of the specimens prepared from plasma treated dentin and the untreated controls (0 sec treatment)

TABLE 2

| | Treatment Time | |
|---|---|---|
| | 0 s | 30 s |
| Bonding Strength | | |
| Average Stress (MPa) | 38.80 | 60.38 |
| Standard Deviation (MPa) | 8.66 | 15.66 |
| Average Modulus (GPa) | 642.49 | 963.45 |
| Standard Deviation (GPa) | 64.48 | 98.05 |
| Fracture Location (%) | | |
| Interface | 84.62% | 50.00% |
| Composite | 15.38% | 50.00% |
| Dentin | 0.00% | 0.00% |
| Zapit | 0.00% | 0.00% |

More specimens cohesively failed in the composite for plasma treated specimens compared to controls, except for the specimens prepared from 300 s plasma treated dentin specimens. Control specimens had adhesive or mixed failures more frequently than the plasma treated specimens. SEM examination of the fractured cross sections showed that large amounts of composite/adhesive were observed on 30 s plasma treated dentin surfaces, which implies the dentin-adhesive interface is stronger than the bulk composite. These trends were also observed with the test specimens that gave higher tensile strength. Plasma treated specimens cohesively failed within the composite more frequently than the control specimens which also implies a stronger interface.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as can be applied to the essential features herein before set forth and as follows in scope of the appended claims.

We claim:

1. A method of increasing bonding strength on a dental restoration site in the mouth of a patient comprising:
   removing material from the dental restoration site to expose a surface comprising dentin;
   generating a cold atmospheric plasma inside the mouth of the patient, said plasma having a brush-like shape;
   after the step of removing material to expose the dentin, applying the cold atmospheric plasma onto the dental restoration site for a period of time between about 30 seconds and 60 seconds to chemically activate the dentin to increase penetration of a dental adhesive into collagen fibrils of the dentin and increase chemical bonding between the collagen fibrils and the dental adhesive;
   wherein said dental adhesive is a composite material and wherein said cold atmospheric plasma comprises argon;
   after the step of applying the plasma, applying the adhesive to the surface; and
   installing a dental restoration on the adhesive-coated surface.

2. The method of claim 1 wherein the dental restoration site comprises a surface of dentin.

3. The method of claim 1 wherein the dental restoration site comprises a surface of enamel.

4. The method of claim 1 wherein the dental restoration site comprises a surface of dental adhesive.

5. The method of claim 1 wherein the dental restoration site comprises a surface of dental composite layers.

6. The method of claim 1 wherein the temperature of the cold atmospheric plasma is between about 35° C. and about 39° C.

7. The method of claim 1 wherein the cold atmospheric plasma comprises plasma gases selected from the group consisting of argon, oxygen, gaseous hydrocarbons, and mixtures thereof.

8. The method of claim 1 where the cold atmospheric plasma is applied to the periphery of a dental restoration site.

9. The method of claim 1, wherein the plasma is applied onto a dental restoration site for a period of time of about 30 seconds.

10. The method of claim 1, wherein said cold atmospheric plasma consists essentially of argon.

11. A method of installing a dental restoration on a tooth inside of a patient's mouth comprising:
   exposing a surface comprising dentin;
   treating the surface with a dentally acceptable acid;
   removing the dentally acceptable acid from the surface;
   providing a plasma generator;
   generating a cold atmospheric plasma inside the mouth of the patient with the plasma generator, said plasma having a brush-like shape;
   after the steps of removing the material from the tooth and removing the acid from the surface, chemically activating the dentin by applying the cold atmospheric plasma onto the surface for a period of time between about 30 seconds and 60 seconds to increase penetration of a dental adhesive into collagen fibrils of the dentin and increase chemical bonding between the collagen fibrils and the dental adhesive;
   after the step of chemically activating the dentin by applying the plasma, coating the dental adhesive on the surface;
   wherein said dental adhesive is a composite material and installing a dental restoration on the adhesive-coated surface.

12. The method of claim 11 comprising, in addition:
   generating a cold atmospheric plasma jet inside the mouth of the patient with the plasma generator; and
   applying the cold atmospheric plasma jet onto the adhesive-coated surface.

13. The method of claim 11 wherein the temperature of the cold atmospheric plasma is between about 35° C. and about 39° C.

14. The method of claim 11 wherein the cold atmospheric plasma comprises plasma gases selected from the group consisting of argon, oxygen, gaseous hydrocarbons, and mixtures thereof.

15. The method of claim 11 wherein the application of cold atmospheric plasma onto the surface results in an increase of carbonyl groups present on the surface for increasing the hydrogen bonding strength between the dental adhesive and collagen fibrils of the dentin.

16. The method of claim 11, wherein said cold atmospheric plasma consists essentially of argon.

17. A method of increasing bonding strength on a dental restoration site in the mouth of a patient comprising:
   exposing a surface comprising dentin;
   treating the surface with a dentally acceptable acid;
   removing the dentally acceptable acid from the surface;
   generating a cold atmospheric plasma inside the mouth of the patient,
   after the steps of removing the material from the tooth and removing the acid from the surface, chemically activating the dentin by applying the cold atmospheric plasma to expose amino acids and increase the exposed surface area of amino acids available for adhesion, the cold atmospheric plasma being applied at a temperature between about 35° C. and 39° C. onto the surface for a period of time between about 10 seconds and 60 seconds;
   after the step of chemically modifying the surface by applying the plasma, coating the dental adhesive on the surface;
   wherein said dental adhesive is a composite material and wherein said cold atmospheric plasma comprises argon; and
   installing a dental restoration on the adhesive-coated surface.

18. The method of claim 17, wherein said cold atmospheric plasma consists essentially of argon.

19. The method of claim 17, wherein the plasma is applied onto a dental restoration site for a period of time of about 30 seconds.

* * * * *